(12) United States Patent
Sembo et al.

(10) Patent No.: US 6,479,542 B2
(45) Date of Patent: Nov. 12, 2002

(54) ECTOPARASITE CONTROL COMPOSITIONS

(75) Inventors: Satoshi Sembo, Nishinomiya (JP); Yasuyori Tanaka, Toyonaka (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/986,099

(22) Filed: Nov. 7, 2001

(65) Prior Publication Data

US 2002/0082294 A1 Jun. 27, 2002

(30) Foreign Application Priority Data

Nov. 9, 2000 (JP) ........................................ 2000-341712
Jul. 5, 2001 (JP) ........................................ 2001-204454

(51) Int. Cl.$^7$ ......................... A01N 43/08; A61K 31/34
(52) U.S. Cl. ....................................... 514/471
(58) Field of Search ........................................ 514/471

(56) References Cited

FOREIGN PATENT DOCUMENTS

| EP | 976328 | * | 2/2000 |
| RU | 2097043 | * | 11/1997 |

* cited by examiner

*Primary Examiner*—Alton N Pryor
(74) *Attorney, Agent, or Firm*—Birch, Stewart, Kolasch & Birch, LLP

(57) ABSTRACT

Provided are ectoparasite control compositions, a method of controlling an ectoparasite and uses of a composition for controlling an ectoparasite. The ectoparasite control compositions comprise a solvent and 1-methyl-2-nitro-3-[(3-tetrahydrofuryl)methyl]guanidine, wherein said solvent contains mainly N-methyl-2-pyrrolidone. The methods of controlling an ectoparasite, comprise applying to a host animal, an ectoparasite control composition which comprises a solvent and 1-methyl-2-nitro-3-[(3-tetrahydrofuryl)methyl]guanidine, wherein said solvent contains mainly N-methyl-2-pyrrolidone.

8 Claims, No Drawings

ECTOPARASITE CONTROL COMPOSITIONS

TECHNICAL FIELD OF THE INVENTION

The present invention relates to ectoparasite control compositions, methods of controlling ectoparasites and uses of a composition for controlling an ectoparasite.

BACKGROUND ARTS

It is well known in the art that when ectoparasites infest a host animal, imidacloprid can be utilized in liquid compositions to control the ectoparasites. In utilizing such liquid compositions to control an ectoparasite, said liquid compositions are sometimes spread or dropped onto the surface of the host animal infested with the ectoparasite. Such liquid compositions utilizing therein imidacloprid, provide an insufficient residual effect over the ectoparasite, as said liquid compositions are utilized to control the ectoparasite over an extended time period.

It is also well known that a pesticidal control effect can be provided by 1-methyl-2-nitro-3-[(3-tetrahydrofuryl)methyl]guanidine. EP 0 976 328 A2 describes an ectoparasite-controlling agent for animals comprising 0.1 to 20% by weight of a neonicotinoid compound and 10 to 95% by weight of a glycol or glycol monoalkyl ether.

SUMMARY OF THE INVENTION

The present invention provides ectoparasite control compositions, ectoparasite control methods and uses for controlling ectoparasite. The ectoparasite control compositions comprise a solvent and 1-methyl-2-nitro-3-[(3-tetrahydrofuryl)methyl]guanidine, wherein said solvent contains mainly N-methyl-2-pyrrolidone. The ectoparasite control methods comprise applying to a host animal, a composition comprising a solvent and 1-methyl-2-nitro-3-[(3-tetrahydrofuryl)methyl]guanidine, wherein said solvent contains mainly N-methyl-2-pyrrolidone.

DETAILED DESCRIPTION OF THE INVENTION

The ectoparasite control compositions of the present invention typically utilize therein a solvent and a effective amount of 1-methyl-2-nitro-3-[(3-tetrahydrofuryl)methyl]guanidine. The solvent in the ectoparasite control compositions contain mainly N-methyl-2-pyrrolidone. The solvent is usually present in the ectoparasite control compositions in an amount of from 40 to 99.9% by weight, wherein said weight percentage is based on the total weight of the provided ectoparasite control compositions. An effective amount of 1-methyl-2-nitro-3-[(3-tetrahydrofuryl)methyl]guanidine in the ectoparasite control compositions can be an amount of from 0.1 to 30% by weight, and preferably is 1 to 30% by weight, wherein said weight percentages are based on the total amount of the provided ectoparasite control compositions.

As used herein, the phrase "contains mainly N-methyl-2-pyrrolidone" means that the provided solvent contains at least 90% by weight of N-methyl-2-pyrrolidone, wherein said weight percentage of N-methyl-2-pyrrolidone is based on the total weight of the solvent utilized in the provided ectoparasite control compositions. For example, such a solvent may consist essentially of N-methyl-2-pyrrolidone. When utilizing said solvent consisting essentially of N-methyl-2-pyrrolidone, the ectoparasite control compositions can comprise the solvent in an amount of from 85 to 99.9% by weight or from 95% to 99.9% by weight, wherein said weight percentages of the solvent are based on the total weight of the provided ectoparasite control composition.

To produce the solvent, N-methyl-2-pyrrolidone may be mixed with various liquid solvents well known in the art. For example, the solvent may involve utilizing therein N-methyl-2-pyrrolidone with alcohols, propylene carboxylate, γ-butyrolactone, water or the like. As examples of the alcohols, there are mentioned glycols, ethyl alcohol, isopropyl alcohol, benzyl alcohol and the like. As examples of the glycols, there are mentioned propylene glycol, hexylene glycol, diethylene glycol, dipropylene glycol, tripropylene glycol, diethylene glycol monoalkyl ether, propylene glycol monoalkyl ether, dipropylene glycol monoalkyl ether, ethylene glycol monophenyl ether and the like.

As needed, the ectoparasite control compositions may additionally comprise an auxiliary. Auxiliaries that may be useful in the ectoparasite control compositions include anti-oxidants, colorants, light stabilizers, sticking agents and the like. When utilizing the auxiliaries in the ectoparasite control compositions, an auxiliary may be present in the ectoparasite control composition in an amount of from 0.0001 to 1% by weight, wherein said weight percentages are based on the total weight of the provided ectoparasite control composition.

When the solvent involves a mixture of N-methyl-2-pyrrolidone and water, a pH adjusting agent may be added to the ectoparasite control compositions, if so desired. As examples of the pH adjusting agent, for example, there can be mentioned citric acid, sodium dihydrogen citrate, sodium hydrogen citrate, potassium hydrogen phosphate, sodium dihydrogen phosphate, ammonium dihydrogen phosphate, ammonium benzoate, sodium benzoate, boric acid, tartaric acid, succinic acid, lactic acid and the like. Such pH adjusting agents are typically utilized in the ectoparasite control compositions to maintain a pH of from 5 to 7 pH. For example, the pH adjusting agent may be present in the ectoparasite control compositions in an amount of from 0.01 to 1% by weight, wherein said weight percentage of the pH adjusting agent is based on the total weight of the water in the ectoparasite control compositions.

As examples of the anti-oxidant, there are mentioned BHT, BHA and the like.

As examples of the colorant, there are mentioned food tar dyes such as food yellow 4 (tartrazine), food green 3 (fast green FCF), food blue 1 ( brilliant blue FCF) and the like.

As examples of the light stabilizers, there are mentioned benzophenone compounds, benzotriazole compounds and the like.

As examples of the sticking agent, there are mentioned cellulose derivatives, starch derivatives, polyacrylates, naturally-occurring polymers, alginic acid salts, gelatin and the like.

The ectoparasite control compositions may also comprise a pesticidal compound in addition to 1-methyl-2-nitro-3-[(3-tetrahydrofuryl)methyl]guanidine. By utilizing such an additional pesticidal compound in the ectoparasite control composition, a more specialized control over the ectoparasite may be provided by the ectoparasite control composition. To provide such a specialized control over the ectoparasite, 0.05 to 50% by weight of the additional pesticidal compound may be added to the ectoparasite control compositions. As examples of such additional pesticidal compounds, there are mentioned pyrethroid compounds such as phenothrin, permethrin, etofenprox, resmethrin, fenpropathrin, cyphenothrin and flumethrin, organophosphorus compounds such as tetrachlorvinphos and fenthion; carbamate compounds such as propoxur, carbaryl and fenobucarb; chitin synthesis inhibitors such as lufenuron, novaluron and chlorfluazuron; juvenile hormone analogs such as pyriproxyfen, fenoxycarb and methoprene; neonicotinoid compounds such as nitenpyram and thiamethoxam; N-phenylpyrazole compounds and the like.

The ectoparasite control compositions can be produced, for example, by mixing the solvent with 1-methyl-2-nitro-3-[(3-tetrahydrofuryl)methyl]guanidine. When also utilizing therein an auxiliary or additional pesticidal compound, the auxiliary or additional pesticidal compound may be mixed with the solvent and 1-methyl-2-nitro-3-[(3-tetrahydrofuryl)methyl]guanidine.

The ectoparasite control compositions are typically regionally applied to the host animal, in order to treat the host animal when infested with an ectoparasite or to prevent the host animal from being infected with an ectoparasite. Exemplary forms of such regional application can involve spot-on applications, pour-on applications and the like. In the spot-on applications the ectoparasite control compositions may be spread or added drop-wise to the skin at a back area between the shoulders of the host animal. In the pour-on applications, the ectoparasite control compositions may be poured along the spine of the host animal.

The application amount to a host animal of the ectoparastie control compositions may change depending on the type of host animal or the type of ectoparasite. For example, the ectoparasite control compositions may be applied to the host animals in an amount such that 0.05 to 1000 mg of 1-methyl-2-nitro-3-[(3-tetrahydrofuryl)methyl]guanidine is applied for every 1 kg of the host animal (i.e., 0.05 to 1000 mg/kg). Alternatively, the ectoparastite control compositions may be applied to the host animal, such that 1-methyl-2-nitro-3-[(3-tetrahydrofuryl)methyl]guanidine is applied in an amount of from 0.1 to 200 mg/kg.

When regionally applying the ectoparasite control compositions to the host animal, the host animal may already be infested with the ectoparasites or may be uninfected with ectoparasites. As examples of such host animals, there are mentioned animals host to ectoparasites, such as animals raised as farm animals or pets. Examples of such host animals include mammal animals, birds and the like. Examples of the mammalian animals include carnivora such as dogs, cats and ferrets; Artiodactyla such as cows, sheeps, goats and swines; rodents (Rodentia) such as mice, rats, hamsters and squirrels; Lagomorpha such as rabbits, primates such as monkeys and the like. Examples of the birds include Anseriformes such as ducks, doves (Columbiformes) such as pigeons, cockatoos (Psittaciformes) such as parrots and the like.

In general, the ectoparasites that can be controlled with the ectoparasite control compositions are arthropods. As examples of such arthropods, there are mentioned Diptera pests such as houseflies (*Musca domestica*), *Musca hervei*, *Musca bezzi, Haematobia irritans, Simulium iwatens, Culicoides oxystoma, Tabanus chrysurus*, common mosquito (*Culex pipiens*) and *Aedes albopictus;* lice pests (Anoplura) such as cattle lice (*Haematopinus eurysternus*) and sheep lice (*Damalinia ovis*); tick pests (Acarina) such as *Haemaphysalis longiconis* and *Boophilus microplus;* fleas (Siphonaptera) such as cat fleas (*Ctenocephalides felis*), dog fleas (*Ctenocephalides canis*) and oriental rat flea (*Xenopsylla cheopis*) and the like.

As an example of the ectoparasite control compositions, there can be mentioned an ectoparasite control composition composed of (a) 0.1 to 30% by weight of 1-methyl-2-nitro-3-[(3-tetrahydrofuryl)methyl]guanidine and (b) 40 to 99.9% by weight of the solvent containing mainly N-methyl-2-pyrrolidone, wherein said weight percentages are based on the total weight of the provided ectoparasite control compositions.

As another example of the ectoparasite control compositions, there can be mentioned an ectoparasite control composition composed of (a) 0.1 to 30% by weight of 1-methyl-2-nitro-3-[(3-tetrahydrofuryl)methyl]guanidine, (b) 40 to 99.9% by weight of the solvent containing mainly N-methyl-2-pyrrolidone and (c) 0.05 to 50% by weight of at least one additional pesticidal compound selected from a pyrethroid compound and a juvenile hormone analog, wherein said weight percentages are based on the total weight of the provided ectoparasite control composition.

EXAMPLES

Formulation Example 1

Nine (9) grams of N-methyl-2-pyrrolidone were added to 1 g of the 1-methyl-2-nitro-3-[(3-tetrahydrofuryl)methyl] guanidine. The resulting mixture is stirred to produce formulation 1.

Formulation Example 2

One (1) gram of 1-methyl-2-nitro-3-[(3-tetrahydrofuryl) methyl]guanidine was added to a solvent to amount to 10 g. The solvent was prepared by mixing N-methyl-2-pyrrolidone with tripropylene glycol at a weight-to-weight ratio of 43:2. The resulting mixture of 1-methyl-2-nitro-3-[(3-tetrahydrofuryl)methyl]guanidine and said solvent was stirred to produce formulation 2.

Formulation Example 3

One-half (0.5) gram of pyriproxyfen and 10 g of 1-methyl-2-nitro-3-[(3-tetrahydrofuryl)methyl]guanidine are added to N-methyl-2-pyrrolidone to amount to 100 g. The resulting mixture is stirred to produce formulation 3.

Formulation Example 4

Forty (40) grams of d-phenothrin, 1.0 g of pyriproxyfen and 10 g of 1-methyl-2-nitro-3-[(3-tetrahydrofuryl)methyl] guanidine are added to N-methyl-2-pyrrolidone to amount to 100 g. The resulting mixture is stirred to produce formulation 4.

Formulation Example 5

Thirty (30) grams of etofenprox, 1.0 g of pyriproxyfen and log of 1-methyl-2-nitro-3-[(3-tetrahydrofuryl)methyl] guanidine are added to N-methyl-2-pyrrolidone to amount to 100 g. The resulting mixture is stirred to produce formulation 5.

Formulation Example 6

Ten (10) grams of fenpropathrin, 1.0 g of pyriproxifen and 10 g of 1-methyl-2-nitro-3-[(3-tetrahydrofuryl)methyl] guanidine are added to N-methyl-2-pyrrolidone to amount to 100 g. The resulting mixture is stirred to produce formulation 6.

Formulation Example 7

Ten (10) grams of flumethrin, 1.0 g of pyriproxifen and log of 1-methyl-2-nitro-3-[(3-tetrahydrofuryl)methyl]

guanidine are added to N-methyl-2-pyrrolidone to amount to 100 g. The resulting mixture is stirred to produce formulation 7.

Formulation Example 8

A solvent is prepared by mixing 8 g of water with N-methyl-pyrrolidone to amount to 89 g. Ten (10) grams of 1-methyl-2-nitro-3-[(3-tetrahydrofuryl)methyl]guanidine and 1 g of pyriproxifen is then added to the solvent to amount to 100 g. The resulting mixture is then stirred to produce formulation 8.

Formulation Example 9

A solvent is prepared by mixing 9 g of diethylene glycol monoethyl ether with N-methyl-2-pyrrolidone to amount to 93.5 g. Five (5) grams of 1-methyl-2-nitro-3-[(3-tetrahydrofuryl)methyl]guanidine, 0.5 g of BHT and 1.0 g of phenothrin are added to the solvent to amount to 100 g. The resulting mixture is then stirred to produce formulation 9.

Formulation Example 10

A solvent is prepared by mixing 8 g of propylene carboxylate and N-methyl-2-pyrrolidone to amount to 94 g. Five (5) grams of 1-methyl-2-nitro-3-[(3-tetrahydrofuryl) methyl]guanidine and 1.0 g of d-phenothrin are added to the solvent The resulting mixture is stirred at to produce formulation 10.

Formulation Example 11

One (1) gram of 1-methyl-2-nitro-3-[(3-tetrahedron) methyl]guanidine and 0.75 g of water are mixed with N-methyl-2-pyrrolidone to amount to 10 g. The resulting mixture is stirred to produce formulation 11.

Comparative Example 1

Three (3) grams of N-methyl-2-pyrrolidone and 6 g of propylene glycol were added to and mixed with 1 g of 1-methyl-2-nitro-3-[(3-tetrahydrofuryl)methyl]guanidine to produce comparative formulation 1.

Comparative Example 2

Three (3) grams of N-methyl-2-pyrrolidone and 6 g of polyethylene glycol 300 were added to and mixed with 1 g of 1-methyl-2-nitro-3-[(3-tetrahydrofuryl)methyl]guanidine to produce comparative formulation 2.

Comparative Example 3

Two and two-fifths (2.4) grams of N-methyl-2-pyrrolidone and 6.6 g of tripropylene glycol were added to and mixed with 1 g of 1-methyl-2-nitro-3-[(3-tetrahydrofuryl)methyl]guanidine to produce comparative formulation 3.

Comparative Example 4

Nine (9) grams of tripropylene glycol were added to and mixed with 1 g of 1-methyl-2-nitro-3-[(3-tetrahydrofuryl) methyl]guanidine to produce comparative formulation 4.

Comparative Example 5

Six and three-fifths (6.6) grams of tripropylene glycol and 2.4 g of isopropyl alcohol were added to and mixed with 1 g of 1-methyl-2-nitro-3-[(3-tetrahydrofuryl)methyl] guanidine to produce comparative formulation 5.

Test Example 1

Cats (bodily weight of 3 kg) were infected, respectively, with 30 adult cat fleas. A day thereafter, 0.4 ml of formulation 1, comparative formulation 1, comparative formulation 2 and a referential formulation were applied, respectively, onto each of the cats infested with the adult cat fleas by a spot-on application. A pipette was utilized to conduct the spot-on application to each of the cats. The referential formulation contained 10% w/v of imidacloprid as an active ingredient and a solvent containing mainly benzyl alcohol (formulation provided by Bayer; product name: advantage spot for cats 40). After the spot-on applications, each of the cats was transferred to a cat cage, was given food and water and was tended to. Three (3) days after said formulations were applied onto the cats by the spot-on application, the cats were treated with a flea removal comb. The number of fleas removed from each of the cats was then counted to determine the first flea infestation rates (%) as well as the first flea control rates (%).

The cats were then given food and water and were further tended to. Fourteen (14) days after said formulations were applied onto the cats by the spot-on application, each of the cats were infested for a second time with 30 adult cat fleas. Each of the cats was transferred to a cat cage, was given food and water and was tended to. Seventeen (17) days after said formulations were applied onto the cats by the spot-on application, the cats were treated with a flea removal comb. The number of fleas removed from each of the cats was then counted to determine the second flea infestation rates (%) as well as the second flea control rates (%).

Additionally, as a control test, a test similar to the above test was conducted with a cat untreated with a formulation. The control flea infestation rate (%) was evaluated for the cat involved in the control test.

The first and second flea control rates were determined by utilizing the equation below.

flea control rate (%)=(C−T)/C×100

C: the flea infestation rate in the control test (%),

T: the flea infestation rate with the formulation application (%)

The control test and the formulation applications were repeated to determine a second round of first and second flea control rates. The flea control rates from the first round were averaged with the second round to provide an average first flea control rate and an average second flea control rate, which are shown below in Table 1 and Table 2.

TABLE 1

| formulation | amount of pesticidal compound | amount of N-methyl-2-pyrrolidone in the solvent | first flea infestation rate (%) | first flea control rate (%) |
|---|---|---|---|---|
| formulation 1 | 10 | 100 | 0 | 100 |
| comparative formulation 1 | 10 | 33 | 1.7 | 98 |
| comparative formulation 2 | 10 | 33 | 0 | 100 |
| referential formulation 1 | 10 *1 | — | 1.7 | 98 |
| control test | — | — | 86.7 | — |

*1 10% w/v of imidacloprid

TABLE 2

| formulation | amount of pesticidal compound | amount of N-methyl-2-pyrrolidone (% w/w) in the solvent | second flea infestation rate (%) | second flea control rate (%) |
|---|---|---|---|---|
| formulation 1 | 10 | 100 | 13.3 | 81.5 |
| comparative formulation 1 | 10 | 33 | 45 | 37.2 |
| comparative formulation 2 | 10 | 33 | 48.3 | 37.2 |
| referential formulation 1 | 10 *1 | — | 1.7 | 32.6 |
| control test | — | — | 71.7 | — |

*1 10% w/v of imidacloprid

Test Example 2

Cats (bodily weight of 3 kg) were infected, respectively, with 30 adult cat fleas. A day thereafter, 0.4 ml of formulation 1, comparative formulation 3, comparative formulation 4 and a comparative formulation 5 were applied, respectively, onto each of the cats infested with the adult cat fleas by a spot-on application. A pipette was utilized to conduct the spot-on application to each of the cats. After the spot-on applications, each of the cats was transferred to a cat cage, was given food and water and was tended to. Three (3) days after said formulations were applied onto the cats by the spot-on application, the cats were treated with a flea removal comb. The number of fleas removed from each of the cats was then counted to determine the first flea infestation rates (%) as well as the first flea control rates (%).

The cats were then given food and water and were farther tended to. Fourteen (14) days after said formulations were applied onto the cats by the spot-on application, each of the cats were infested for a second time with 30 adult cat fleas. Each of the cats was transferred to a cat cage, was given food and water and was tended to. Seventeen (17) days after said formulations were applied onto the cats by the spot-on application, the cats were treated with a flea removal comb. The number of fleas removed from each of the cats was then counted to determine the second flea infestation rates (%) as well as the second flea control rates (%).

Additionally, as a control test, a test similar to the above test was conducted with a cat untreated with a formulation. The control flea infestation rate (%) was evaluated for the cat involved in the control test.

The first and second flea control rates were determined by utilizing the equation below.

flea control rate (%)=(C−T)/C×100

C: the flea infestation rate in the control test (%),

T: the flea infestation rate with the formulation application (%)

The control test and the formulation applications were repeated to determine a second round of first and second flea control rates. The flea control rates from the first round were averaged with the second round to provide an average first flea control rate and an average second flea control rate, which are shown below in Table 1 and Table 2.

TABLE 3

| formulation | amount of pesticidal compound | amount of N-methyl-2-pyrrolidone (% w/w) in the solvent | first flea infestation rate (%) | first flea control rate (%) |
|---|---|---|---|---|
| formulation 1 | 10 | 100 | 0.0 | 100.0 |
| comparative formulation 3 | 10 | 27 | 0.0 | 100.0 |
| comparative formulation 4 | 10 | — | 0.0 | 100.0 |
| comparative formulation 5 | 10 | — | 0.0 | 100.0 |
| control test | — | — | 73.3 | — |

TABLE 4

| formulation | amount of pesticidal compound | amount of N-methyl-2-pyrrolidone (% w/w) in the solvent | second flea infestation rate (%) | second flea control rate (%) |
|---|---|---|---|---|
| formulation 1 | 10 | 100 | 15.0 | 83.0 |
| comparative formulation 3 | 10 | 27 | 61.7 | 30.1 |
| comparative formulation 4 | 10 | — | 81.7 | 7.5 |
| comparative formulation 5 | 10 | — | 76.7 | 13.1 |
| control test | — | — | 88.3 | — |

Test Example 3

A cat (bodily weight of 3 kg) was infected with 30 adult cat fleas. A day thereafter, 0.4 ml of formulation 1 was applied onto the cat infested with the adult cat fleas by a spot-on application. A pipette was utilized to conduct the spot-on application to the cat. After the spot-on application, the cat was transferred to a cat cage, was given food and water and was tended to. Three (3) days after said formulation was applied onto the cat by the spot-on application, the cat was treated with a flea removal comb. The number of fleas removed from the cat was then counted to determine the first flea infestation rates (%) as well as the first flea control rates (%).

The cat was then given food and water and was further tended to. Fourteen (14) days after said formulations was applied onto the cat by the spot-on application, the cat was infested for a second time with 30 adult cat fleas. The cat was transferred to a cat cage, was given food and water and was tended to. Seventeen (17) days after said formulation was applied onto the cat by the spot-on application, the cat was treated with a flea removal comb. The number of fleas removed from the cat was then counted to determine the second flea infestation rates (%) as well as the second flea control rates (%).

Additionally, as a control test, a test similar to the above test was conducted with a cat untreated with a formulation. The control flea infestation rate (%) was evaluated for the cat involved in the control test.

The first and second flea control rates were determined by utilizing the equation below.

flea control rate (%)=(C−T)/C×100

C: the flea infestation rate in the control test (%),

T: the flea infestation rate with the formulation application (%)

The control test and the formulation application were repeated to determine a second round of first and second flea control rates. The flea control rates from the first round were averaged with the second round to provide an average first flea control rate and an average second flea control rate, which are shown below in Table 1 and Table 2.

TABLE 5

| formulation | amount of pesticidal compound | amount of N-methyl-2-pyrrolidone (% w/w) in the solvent | first flea infestation rate (%) | first flea control rate (%) |
|---|---|---|---|---|
| formulation 1 | 10 | 100 | 0.0 | 100.0 |
| control test | — | — | 85.6 | — |

TABLE 6

| formulation | amount of pesticidal compound | amount of N-methyl-2-pyrrolidone (% w/w) in the solvent | second flea infestation rate (%) | second flea control rate (%) |
|---|---|---|---|---|
| formulation 1 | 10 | 100 | 17.8 | 81.4 |
| control test | — | — | 95.6 | — |

The results above evidence that the ectoparasite control compositions can provide a control of an ectoparasite over an extended period of time.

What is claimed is:

1. An ectoparasite control composition consisting essentially of:
   (a) a solvent and
   (b) 1-methyl-2-nitro-3-[(3-tetrahydrofuryl)methyl] guanidine,
   wherein said solvent contains mainly N-methyl-2-pyrrolidone.

2. The ectoparasite control composition according to claim 1, wherein said ectoparasite control composition consists essentially of:
   (a) 40 to 99.9% by weight of said solvent, and
   (b) 1-methyl-2-nitro-3-[(3-tetrahydrofuryl)methyl]-guanidine,
   wherein said solvent contains mainly N-methyl-2-pyrrolidone and said weight percentage is based on the total weight of the ectoparasite control composition.

3. An ectoparasite control composition consisting essentially of:
   (a) a solvent,
   (b) 1-methyl-2-nitro-3-[(3-tetrahydrofuryl)methyl] guanidine, and
   (c) at least one auxiliary selected from an anti-oxidant, a colorant, a light stabilizer, a sticking agent, and pH adjusting agent,
   wherein said solvent contains mainly N-methyl-2-pyrrolidone.

4. An ectoparasite control composition consisting essentially of:
   (a) a solvent,
   (b) 1-methyl-2-nitro-3-[(3-tetrahydrofuryl)methyl] guanidine,
   (c) at least one auxiliary selected from an anti-oxidant, a colorant, a light stabilizer, a sticking agent, and pH adjusting agent, and
   (d) at least one pesticidal compound selected from the group consisting of a pyrethroid compound, an organophosphorous compound, a carbamate compound, a chitin synthesis inhibitor, a juvenile hormone analog, a neonicotinoid compound and N-phenylpyrazole,
   wherein said solvent contains mainly N-methyl-2-pyrrolidone.

5. A method of controlling an ectoparasite, comprising:
   applying to a host animal, an ectoparasite control composition consisting essentially of:
   (a) a solvent, and
   (b) 1-methyl-2-nitro-3-[(3-tetrahydrofuryl)methyl] guanidine,
   wherein said solvent contains mainly N-methyl-2-pyrrolidone.

6. The method according to claim 5, wherein the ectoparasite control composition consists essentially of:
   (a) 40 to 99.9% by weight of said solvent, and
   (b) 1-methyl-2-nitro-3-[(3-tetrahydrofuryl)methyl]-guanidine,
   wherein said solvent contains mainly N-methyl-2-pyrrolidone and said weight percentage is based on the total weight of the ectoparasite control composition.

7. An ectoparasite control composition consisting essentially of:
   (a) a solvent,
   (b) 1-methyl-2-nitro-3-[(3-tetrahydrofuryl)methyl] guanidine, and
   (c) at least one pesticidal compound selected from the group consisting of a pyrethroid compound, an organophosphorous compound, a carbamate compound, a chitin synthesis inhibitor, a juvenile hormone analog, a neonicotinoid compound and N-phenylpyrazole,
   wherein said solvent contains mainly N-methyl-2-pyrrolidone.

8. A method of controlling an ectoparasite, comprising:
   applying to a host animal, an ectoparasite control composition consisting essentially of:
   (a) a solvent,
   (b) 1-methyl-2-nitro-3-[(3-tetrahydrofuryl)methyl] guanidine, and
   (c) at least one pesticidal compound selected from the group consisting of a pyrethroid compound, an organophosphorous compound, a carbamate compound, a chitin synthesis inhibitor, a juvenile hormone analog, a neonicotinoid compound and N-phenylpyrazole,
   wherein said solvent contains mainly N-methyl-2-pyrrolidone.

* * * * *